US011896435B2

(12) United States Patent
Takahashi et al.

(10) Patent No.: US 11,896,435 B2
(45) Date of Patent: Feb. 13, 2024

(54) ULTRASOUND DIAGNOSTIC APPARATUS AND EXAMINATION METHOD

(71) Applicant: Canon Medical Systems Corporation, Otawara (JP)

(72) Inventors: Hiroki Takahashi, Nasushiobara (JP); Tomohisa Imamura, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 382 days.

(21) Appl. No.: 17/061,719

(22) Filed: Oct. 2, 2020

(65) Prior Publication Data

US 2021/0137501 A1 May 13, 2021

(30) Foreign Application Priority Data

Oct. 4, 2019 (JP) ................................ 2019-183746

(51) Int. Cl.
  *A61B 8/14* (2006.01)
  *A61B 8/08* (2006.01)
  *A61B 8/06* (2006.01)
  *A61B 8/00* (2006.01)

(52) U.S. Cl.
  CPC .............. *A61B 8/5276* (2013.01); *A61B 8/06* (2013.01); *A61B 8/145* (2013.01); *A61B 8/5207* (2013.01); *A61B 8/5223* (2013.01); *A61B 8/4488* (2013.01); *A61B 8/488* (2013.01)

(58) Field of Classification Search
  CPC ......... A61B 8/5276; A61B 8/06; A61B 8/145; A61B 8/5207; A61B 8/5223; A61B 8/4488; A61B 8/488
  See application file for complete search history.

(56) References Cited

U.S. PATENT DOCUMENTS

| 6,296,612 B1 * | 10/2001 | Mo ...................... G01S 15/8981 |
| | | 600/455 |
| 2017/0265845 A1 * | 9/2017 | Tsushima ................. A61B 8/06 |
| 2020/0022679 A1 | 1/2020 | Imamura | |

FOREIGN PATENT DOCUMENTS

| JP | 2006-320399 A | 11/2006 |
| JP | 2009-112491 A | 5/2009 |
| JP | 2013000414 A * | 1/2013 |
| JP | 2020-018845 A | 2/2020 |

* cited by examiner

*Primary Examiner* — Mark D Remaly
(74) *Attorney, Agent, or Firm* — Oblon, McClelland, Maier & Neustadt, L.L.P.

(57) ABSTRACT

According to one embodiment, an ultrasound diagnostic apparatus includes processing circuitry. The processing circuitry forms a first transmission beam in a plurality of directions belonging to a first group, forms at least one first reception beam, forms a second transmission beam in a plurality of directions belonging to a second group, after an elapse of a time from performing a scan for the first group, forms at least one second reception beam, applies a wall filter to reception signals obtained by the first and the second reception beams, calculates bloodstream information based on the filtered reception signals, and generates image data based on the calculated bloodstream information.

15 Claims, 10 Drawing Sheets

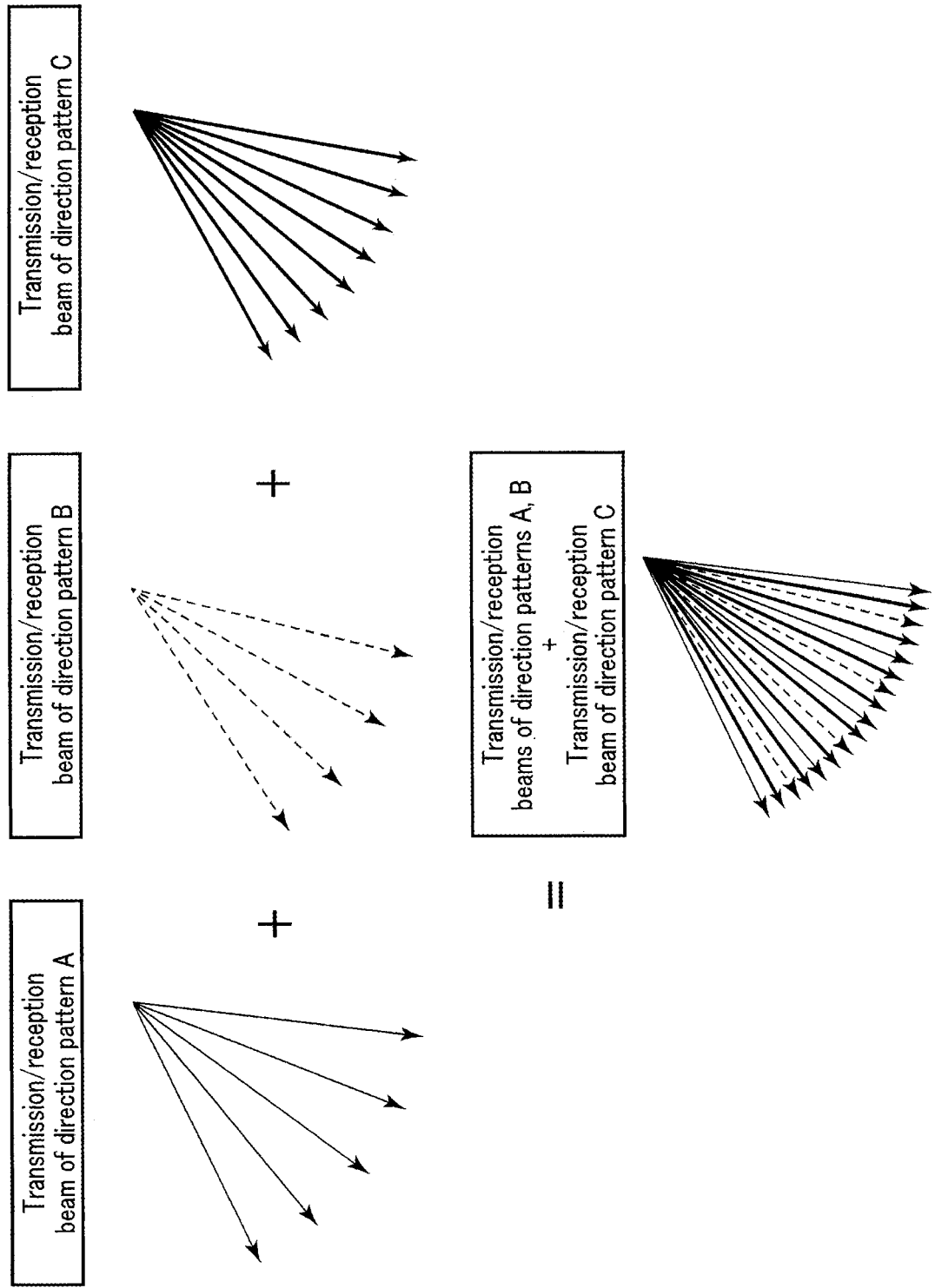
F I G. 5

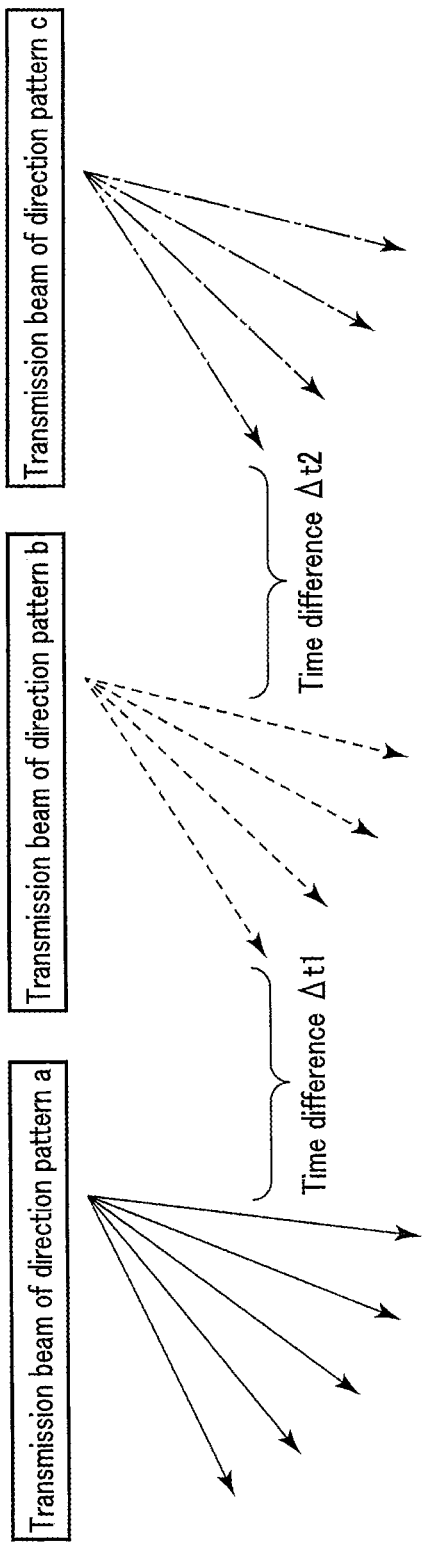
F I G. 11

ULTRASOUND DIAGNOSTIC APPARATUS AND EXAMINATION METHOD

CROSS-REFERENCE TO RELATED APPLICATIONS

This application is based upon and claims the benefit of priority from Japanese Patent Applications No. 2019-183746, filed Oct. 4, 2019; and No. 2020-165947, filed Sep. 30, 2020; the entire contents of both of which are incorporated herein by reference.

FIELD

Embodiments described herein relate generally to an ultrasound diagnostic apparatus and an examination method.

BACKGROUND

Doppler imaging representing a color Doppler method is known widely as a bloodstream visualization technique using ultrasound waves. In Doppler imaging, a bloodstream image is generated by analyzing a frequency shift that is received when a reflected wave signal of an ultrasound pulse emitted by an ultrasound diagnostic apparatus is reflected by a moving object such as a bloodstream or cardiac wall, etc. Since an intensity of a reflected wave from a bloodstream is weaker than an intensity of a reflected wave from tissue other than the bloodstream, filter processing (so-called wall motion filtering) for reducing signals with small frequency shifts is performed to suppress signal components from tissues other than the bloodstream.

The frequency shift that the reflected wave signal undergoes depends on a velocity component in an ultrasound transmission direction. Therefore, a bloodstream with a small velocity component in the ultrasound transmission direction, such as a reflected wave signal reflected by a bloodstream flowing orthogonally to the ultrasound transmission direction, will be suppressed by the filter processing.

Furthermore, since blood is an assembly of scatterers in sizes equal to or smaller than an ultrasound wavelength, reflected wave signals reflected by the scatterers may receive interference. Therefore, scattered signals from blood form spatially irregular amplitude distributions referred to as speckle patterns; that is, form amplitude distributions where local amplitude drops occur. Furthermore, since frequencies of ultrasound waves vary locally, even if the bloodstream velocity and the ultrasound pulse transmission direction are the same, there may be differences in the observed frequency shift amount, which may cause differences in amplitudes of reception signals.

Therefore, in Doppler imaging, the direction in which the bloodstream flows and/or the presence of scatterers in the blood may cause luminance irregularities in a bloodstream image.

BRIEF DESCRIPTION OF THE DRAWINGS

FIG. 5 is a diagram showing a scanning line direction realized by the transmission/reception beams of direction patterns A, B, and C.

FIG. 11 is a diagram showing directions in which transmission beams are formed in a third modification.

DETAILED DESCRIPTION

In general, according to one embodiment, an ultrasound diagnostic apparatus includes processing circuitry. The processing circuitry forms a first transmission beam in a plurality of directions belonging to a first direction group, forms at least one first reception beam for each of the first transmission beams, forms a second transmission beam in a plurality of directions belonging to a second direction group, after an elapse of a predetermined time from performing a scan for the first direction group, forms at least one second reception beam for each of the second transmission beams, applies a wall filter to reception signals obtained by the first reception beams and the second reception beams, calculates bloodstream information based on the filtered reception signals, and generates image data based on the calculated bloodstream information.

Embodiments will be described below with reference to the accompanying drawings.

First Embodiment

Figure 1:
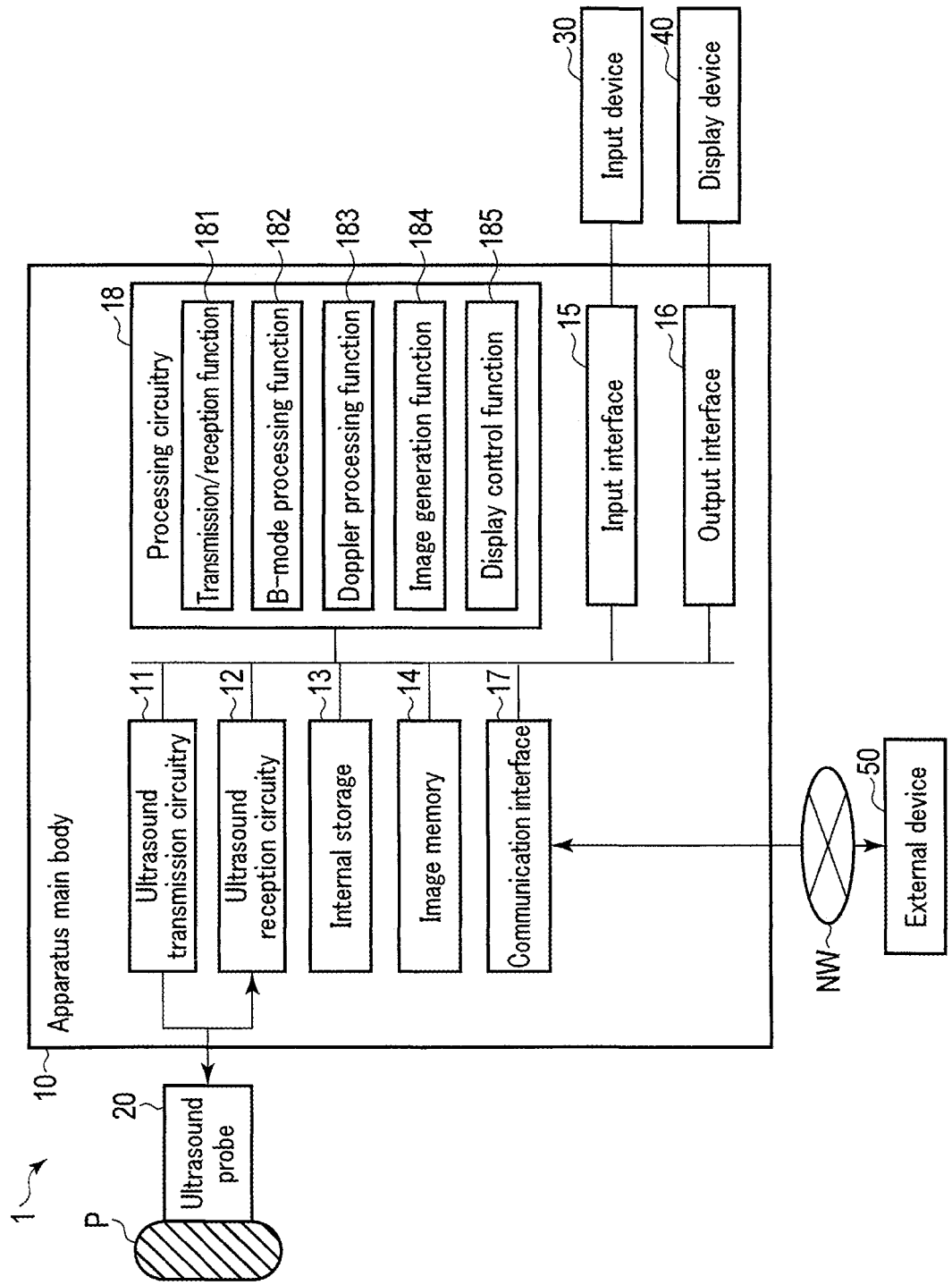
FIG. 1 is a block diagram showing a functional configuration of an ultrasound diagnostic apparatus according to a first embodiment.

FIG. 1 is a block diagram showing an example of a functional configuration of an ultrasound diagnostic apparatus 1 according to a first embodiment. The ultrasound diagnostic apparatus 1 shown in FIG. 1 includes an apparatus main body 10 and an ultrasound probe 20. The apparatus main body 10 is connected to an input device 30 and a display device 40. The apparatus main body 10 is connected to an external device 50 via a network NW.

The ultrasound probe 20 executes ultrasound scanning in a scan area of a living body P, which is the subject, under the control of, for example, the apparatus main body 10. The ultrasound probe 20 includes, for example, a plurality of piezoelectric transducers, a matching layer provided in each of the piezoelectric transducers, and a backing material that prevents ultrasound waves from propagating backward from the piezoelectric transducers. The ultrasound probe 20 is detachably connected to the apparatus main body 10. The ultrasound probe 20 may be provided with a button which is pressed when offset processing is performed or when an ultrasound image freezes.

The ultrasound probe 20 is, for example, a one-dimensional array linear probe in which a plurality of ultrasound transducers are arranged in a predetermined direction, a two-dimensional array probe in which a plurality of piezoelectric transducers are arranged in the form of a matrix, or a mechanical four-dimensional probe capable of executing an ultrasound scan while mechanically flapping a piezoelectric transducer line in directions orthogonal to the alignment direction.

The piezoelectric transducers generate an ultrasound wave based on a drive signal supplied from ultrasound transmission circuitry 11 to be described later, which is included in the apparatus main body 10. An ultrasound wave is thereby transmitted from the ultrasound probe 20 to the living body P. When an ultrasound wave is transmitted from the ultrasound probe 20 to the living body P, the transmitted ultrasound wave is sequentially reflected on the acoustic impedance discontinuous surface of the body tissue of the living body P, and is received as a reflected wave signal by a plurality of piezoelectric elements. The amplitude of the received reflected wave signal depends on the difference in acoustic impedance on the discontinuous surface from which the ultrasound wave is reflected. If the transmitted ultrasound pulse is reflected from the surface of, for example, a moving bloodstream or cardiac wall, the frequency of the resultant reflected wave signal will be shifted due to the Doppler effect, with the shift depending on the velocity component in the ultrasound transmission direction of the moving object. The ultrasound probe 20 receives the reflected wave signal from the living body P, and converts it into an electrical signal.

FIG. 1 only shows a connection relationship between the ultrasound probe 20 used for ultrasound scanning and the apparatus main body 10. However, a plurality of ultrasound probes may be connected to the apparatus main body 10. Which of the connected ultrasound probes is to be used for the ultrasound scanning can be selected freely by a switching operation.

The apparatus main body 10 generates an ultrasound image based on the reflected wave signal received by the ultrasound probe 20. The apparatus main body 10 includes ultrasound transmission circuitry 11, ultrasound reception circuitry 12, internal storage 13, an image memory 14, an input interface 15, an output interface 16, a communication interface 17, and processing circuitry 18.

The ultrasound transmission circuitry 11 is a processor that supplies a drive signal to the ultrasound probe 20. The ultrasound transmission circuitry 11 is realized by, for example, a pulse generator, transmission delay circuitry, and pulser circuitry. The pulse generator repeatedly generates a rate pulse for forming a transmission ultrasound wave at a predetermined pulse repetition frequency (PRF). The transmission delay circuitry provides each rate pulse generated by the pulse generator with a delay time for each piezoelectric transducer, which is necessary for converging the ultrasound wave generated by the ultrasound probe 20 into a beam form and determining a transmission directivity. The transmission direction or the transmission delay time for determining the transmission direction is stored in the internal storage 13, and is referred to upon transmission. The pulser circuitry applies a drive signal (drive pulse) to the multiple ultrasound transducers of the ultrasound probe 20 at a timing based on the rate pulse. By varying the delay time provided to each rate pulse by the transmission delay circuitry, the transmission direction from the piezoelectric transducer surface can be freely adjusted.

The ultrasound transmission circuitry 11 has a function of instantly changing the transmission frequency, transmission drive voltage, or the like to execute a predetermined scan sequence based on an instruction from the processing circuitry 18. In particular, the function of changing the transmission drive voltage is realized by, for example, linear-amplifier-type originating circuitry capable of instantly changing the value or a mechanism for electrical switching between a plurality of power-supply units.

The ultrasound reception circuitry 12 is a processor that performs various types of processing on the reflected wave signal received by the ultrasound probe 20, and thereby generates a reception signal. The ultrasound reception circuitry 12 may be realized by, for example, a preamplifier, an A/D converter, a demodulator, and a beam former.

The preamplifier performs gain correction processing by amplifying the reflected wave signal received by the ultrasound probe 20 for each channel. At this time, the preamplifier changes a gain value in accordance with, for example, a predetermined time response. The time response of the gain applied to the reception signal at the preamplifier is stored in the internal storage 13. The A/D converter converts the gain-corrected reflected wave signal into a digital signal. The demodulator demodulates the digital signal, thereby converting the digital signal into an in-phase signal (I-signal; I: In-phase) and a quadrature signal (Q-signal; Q: Quadrature-phase). The beam former provides the I-signal and Q-signal (hereinafter referred to as an IQ signal) with a delay time necessary for determining a reception directivity. The beam former sums IQ signals each provided with a delay time. Through the processing performed by the beam former, a reception signal is generated in which a reflection component from a direction corresponding to the reception directivity is emphasized.

The ultrasound transmission circuitry 11 and ultrasound reception circuitry 12 are examples of a transmitter/receiver.

At least a part of the ultrasound transmission circuitry 11 and the ultrasound reception circuitry 12 may be shared. If software beamforming is adopted by using reflected wave signals, for example, at least part of the function of the ultrasound reception circuitry 12 (e.g., reception beamforming function) may be realized by the processing circuitry 18 instead, which will be described later. That is, the processing circuitry 18 may also be an example of the transmitter/receiver.

At least part of the ultrasound transmission circuitry 11 and the ultrasound reception circuitry 12 may be provided in the ultrasound probe 20.

The internal storage 13 includes, for example, a magnetic or optical storage medium, or a processor-readable storage medium such as a semiconductor memory. The internal storage 13 stores, for example, a program for realizing ultrasound transmission/reception. The internal storage 13 also stores various types of data such as diagnostic information, a scan sequence, a diagnostic protocol, an ultrasound transmission/reception condition, a signal processing condition, an image generation condition, an image processing condition, a body mark generation program, a display condition, and a conversion table or the like that presets, for each diagnostic site, the range of color data used for visualization. The programs and various types of data may be stored in advance in, for example, the internal storage 13, or may be stored and distributed in a non-transitory storage medium, read from the non-transitory storage medium, and installed in the internal storage 13.

The internal storage 13 stores the reception signal generated in the ultrasound reception circuitry 12 and various ultrasound image data items, etc. generated in the processing circuitry 18, in accordance with an operation input via the input interface 15. The internal storage 13 may transfer the stored data to the external device 50, etc. via the communication interface 17.

The internal storage 13 may be a driving device, etc. that reads and writes various types of information with respect to a portable storage medium such as a CD-ROM drive, DVD drive, or flash memory. The internal storage 13 may also be designed to write the stored data onto a portable storage medium and store the data into the external device 50 by way of a portable storage medium.

The image memory 14 includes, for example, a magnetic or optical storage medium, or a processor-readable storage medium such as a semiconductor memory. The image memory 14 stores therein image data corresponding to a plurality of frames immediately before a freeze operation that is input via the input interface 15. The image data stored in the image memory 14 is, for example, sequentially displayed (as moving images).

The internal storage 13 and the image memory 14 need not necessarily be realized by independent storage devices. The internal storage 13 and the image memory 14 may be realized by a single storage device. Each of the internal storage 13 and the image memory 14 may be realized by a plurality of storage devices.

The input interface 15 receives various commands from an operator through the input device 30. The input device 30 may include a mouse, a keyboard, panel switches, slider switches, a track ball, a rotary encoder, an operation panel, a touch command screen (TCS), and the like. The input interface 15 is coupled to the processing circuitry 18 via a bus, for example, thereby converting an operation command that is input by the operator to an electric signal, and outputting this electric signal to the processing circuitry 18. The input interface 15 is not limited to a component that is coupled to a physical operation component such as a mouse and keyboard. Examples of the input interface may include circuitry that is configured to receive an electric signal corresponding to an operation command input from an external input device that is provided separately from the ultrasound diagnostic apparatus 1 and to output this electric signal to the processing circuitry 18.

The output interface 16 is an interface for outputting, for example, an electric signal from the processing circuitry 18 to the display device 40. The display device 40 may be any display such as a liquid crystal display, an organic EL display, an LED display, a plasma display, or a CRT display. The output interface 16 is coupled to the processing circuitry 18 via the bus, for example, and outputs an electric signal from the processing circuitry 18 to the display device.

The communication interface 17 is coupled to the external device 50 via, for example, the network NW, and performs data communications with the external device 50.

The processing circuitry 18 is, for example, a processor that functions as a nerve center of the ultrasound diagnostic apparatus 1. The processing circuitry 18 executes the program stored in the internal storage 13, thereby realizing the functions corresponding to the program. The processing circuitry 18 may include, for example, a transmission/reception function 181, B-mode processing function 182, Doppler processing function 183, image generation function 184, and display control function 185. The present embodiment explains a case in which a single processor realizes the transmission/reception function 181, B-mode processing function 182, Doppler processing function 183, image generation function 184, and display control function 185. However, the embodiment is not limited thereto. For example, a plurality of independent processors may be combined to configure the processing circuitry, and the transmission/reception function 181, B-mode processing function 182, Doppler processing function 183, image generation function 184, and display control function 185 may be realized by executing programs of each processor. Dedicated hardware circuitry capable of executing each function may also be incorporated.

The transmission/reception function 181 is a function to control the ultrasound transmission circuitry 11 and the ultrasound reception circuitry 12, thereby enabling the ultrasound probe 20 to perform ultrasound scanning. With the transmission/reception function 181, the processing circuitry 18 controls the transmission of ultrasound waves by the ultrasound transmission circuitry 11 and the reception of reflected wave signals by the ultrasound reception circuitry 12, in accordance with the information read from the internal storage 13.

Specifically, the processing circuitry 18 controls the ultrasound transmission circuitry 11 so that the ultrasound transmission circuitry 11 can apply, to the ultrasound transducers, drive signals to which respective delay times are given. Each of the ultrasound transducers transmits ultrasound waves at a timing based on the given delay time. The ultrasound waves transmitted from the ultrasound transducers are combined into a transmission beam.

Furthermore, the processing circuitry 18 controls the ultrasound transmission circuitry 11 so that a plurality of patterns of directions in which the transmission beams are formed exist, with a predetermined time difference therebetween, in an imaging region of interest (ROI) set in a scan area. Specifically, for example, the processing circuitry 18 controls the ultrasound transmission circuitry 11 to form a transmission beam in direction pattern A to which a plurality of directions belong, and, after providing a predetermined time difference, in direction pattern B to which a plurality of directions belong. The directions included in direction pattern A and the directions included in direction pattern B are respectively different directions. The direction patterns may also be referred to as direction groups. A predetermined time difference indicates, for example, a time required for the distributed state of most of the scatterers included in the blood to be newly replaced.

Figure 2:
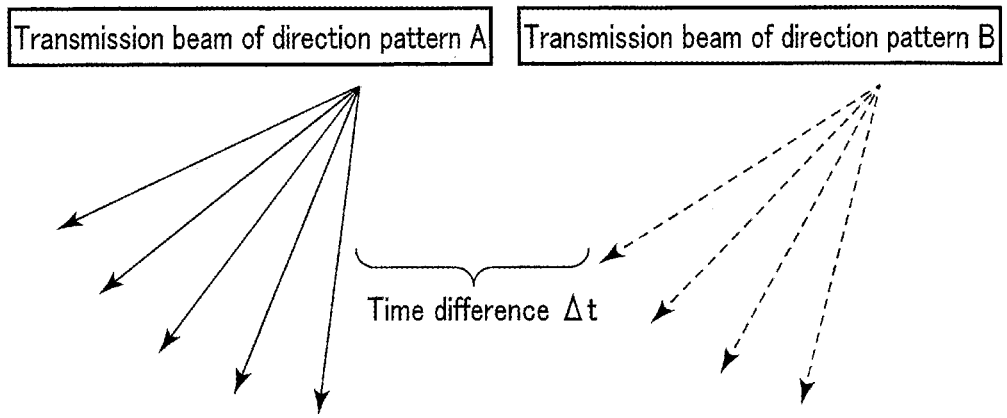
FIG. 2 is a diagram showing a direction in which a transmission beam generated by ultrasound transmission circuitry shown in FIG. 1 is formed.

FIG. 2 is a schematic diagram showing an example of a direction in which the transmission beam generated by the ultrasound transmission circuitry 11 shown in FIG. 1 is formed. According to FIG. 2, transmission beams are sequentially formed from a first direction to a fifth direction belonging to direction pattern A. Transmission beams are also sequentially formed from a first direction to a fourth direction belonging to direction pattern B. The five directions belonging to direction pattern A and the four directions belonging to direction pattern B are respectively different directions. Furthermore, a stand-by time of $\Delta t$ exists between reception of a reflected wave signal with respect to a transmission beam formed in the last direction belonging to direction pattern A, that is, the fifth direction of direction pattern A, and formation of a transmission beam in the first direction belonging to direction pattern B, that is, the first direction of direction pattern B. FIG. 2 explains an example of a transmission beam in a sector-type electronic scan; however, it is not limited thereto. The scan according to the present embodiment may be a convex scan or a linear scan. Furthermore, the transmission beam may be a non-convergent ultrasound beam such as a plane wave or a diffuse wave.

Furthermore, for example, the processing circuitry 18 controls the ultrasound reception circuitry 12 so as to generate at least one reception signal by providing each of the reflected wave signals received by the ultrasound probe 20 with a delay time in consideration of the reception directivity, and summing up the reflected wave signals to which the delay time is added. In this manner, at least one reception beam is formed with respect to a single transmission beam. The number of reception beams formed with respect to one transmission beam is not limited to one, and may be more than one.

The B-mode processing function 182 is a function to generate B-mode data based on a reception signal received from the ultrasound reception circuitry 12. Specifically, by the B-mode processing function 182, the processing circuitry 18 performs envelope detection processing, logarithmic compression processing, and the like on the reception signal received from the ultrasound reception circuitry 12 to generate data (B-mode data) that expresses signal intensity by brightness. The generated B-mode data is stored in a raw data memory (not shown) as B-mode raw data on a two-dimensional ultrasound scanning line (raster).

The Doppler processing function 183 is a function of analyzing the frequency of the reception signal received from the ultrasonic reception circuitry 12 to thereby generate data (Doppler data) relating to bloodstream information based on a Doppler effect of a moving object in an imaging ROI set in the scan area. The bloodstream information includes average velocity, dispersion, and power of the bloodstream in the subject, or a combination thereof. The generated Doppler data is stored in a raw data memory (not shown in the drawings) as two-dimensional Doppler raw data on an ultrasound scanning line.

Specifically, by the Doppler processing function 183, the processing circuitry 18 executes, for example, filter processing, combining processing, autocorrelation processing, and arithmetic processing.

In the filter processing, a wall filter is applied to data strings relating to a reflected wave signal continuously reflected from the same position. The filter processing is an example of a filtering unit. This allows signals (clutter signals) related to any stationary tissue or slow-moving tissue to be suppressed, and bloodstream-related signals to be extracted. As the wall filter, for example, a moving target indicator (MTI) filter is used. As the MTI filter, for example, a butterworth infinite impulse response (IIR) filter or a polynomial regression filter in which filter coefficients are fixed is used.

In the combining processing, signals on which the filter processing is performed are weighted for each direction pattern and combined. The combining processing is an example of a combining unit. In this manner, a signal of a direction pattern that is different from the actually scanned direction pattern is generated.

In the autocorrelation processing, an autocorrelation operation is performed with respect to signals on which the filter processing is performed and with respect to signals that are combined. Specifically, for example, the processing circuitry 18 calculates an autocorrelation value by obtaining a complex conjugate of an IQ signal of the latest pulse from which a clutter signal is removed and an IQ signal of a pulse before.

In the arithmetic processing, the bloodstream information is calculated based on the signals on which the above processing is performed. The arithmetic processing is an example of an operation unit. Specifically, for example, the processing circuitry 18 calculates an average velocity and dispersion from the autocorrelation value calculated by the autocorrelation processing. Furthermore, the processing circuitry 18 calculates the power by summing the square of an absolute value of a real part and the square of an absolute value of an imaginary part of the IQ signal.

The processing performed by the processing circuitry 18 through the Doppler processing function 183 is not limited to the filter processing, combining processing, autocorrelation processing, and arithmetic processing. In addition to the above processing, the processing circuitry 18 may execute, for example, blank processing, space-smoothing processing, and a time-direction-smoothing processing. Furthermore, in the case where the direction pattern is not to be increased for simulation, the combining processing does not have to be implemented.

The image generation function 184 is a function of generating various types of ultrasound image data based on the data generated by the B-mode processing function 182 and/or Doppler processing function 183, and is an example of an image generation unit. Specifically, by the image generation function 184, the processing circuitry 18 executes, for example, a raw-pixel conversion, such as a coordinate conversion corresponding to the mode of the ultrasound scan by the ultrasonic probe 20, on B-mode raw data stored in the raw data memory to generate B-mode image data consisting of pixels.

The processing circuitry 18 also executes, for example, a raw-pixel conversion on Doppler raw data stored in the raw data memory to generate Doppler image data that visualizes bloodstream information. The Doppler image data is average velocity image data, dispersion image data, power image data, or image data obtained by a combination thereof.

The display control function 185 is a function of causing the display device 40 to display images based on various types of ultrasound image data generated by the image generation function 184. Specifically, for example, by the display control function 185, the processing circuitry 18 controls the display device 40 to display an image based on the B-mode image data, the Doppler image data, or the ultrasound image data including both types of data, generated by the image generation function 184.

For example, by the display control function 185, the processing circuitry 18 converts (scan-converts) a scanning line signal sequence of an ultrasound scan into a scanning line signal sequence of a video format representatively used by television, etc. to generate display image data. The processing circuitry 18 may also perform various types of processing, such as dynamic range, brightness, contrast, γ curve corrections, and an RGB conversion, on the display image data. The processing circuitry 18 may also add supplementary information, such as textual information of various parameters, a scale, or a body mark, to the display image data. The processing circuitry 18 may also generate a user interface (graphical user interface (GUI)) to allow the operator to input various instructions through the input device, and cause the display device 40 to display the GUI.

An example of measurement processing performed by the ultrasound diagnostic apparatus 1 configured in the above manner will now be explained.

Figure 3:
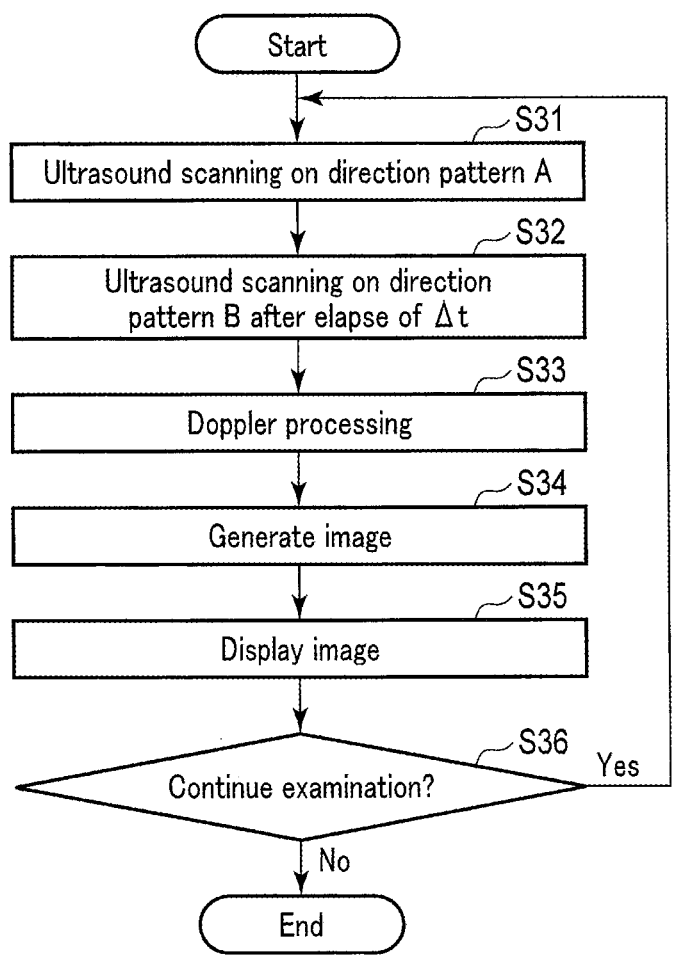
FIG. 3 is a flowchart showing operations of processing circuitry when displaying an ultrasound image on a display device of the ultrasound diagnostic apparatus shown in FIG. 1.

FIG. 3 is a flowchart showing an example of operations of the processing circuitry 18 when displaying an ultrasound image on a display device 40 of the ultrasound diagnostic apparatus 1 shown in FIG. 1. In the explanation of FIG. 3, an imaging ROI for generating Doppler image data is assumed to be set in a scan area via the input interface 15.

First, the operator selects, for example, a bloodstream imaging mode, and inputs a start instruction to start the selected bloodstream imaging mode via the input interface 15. When the start instruction to start the bloodstream imaging mode is input, the processing circuitry 18 executes the transmission/reception function 181. By the transmission/reception function 181, the processing circuitry 18 reads, for example, a scan sequence for the bloodstream imaging mode from the internal storage 13. The processing circuitry 18 executes a scan based on the read scan sequence.

For example, based on the scan sequence, the processing circuitry 18 reads an ultrasound transmission/reception condition for the color Doppler method from the internal storage 13. In the explanation of FIG. 3, the ultrasound transmission/reception condition includes, for example, information for forming transmission beams in direction patterns A and B, and information of a time difference between a scan executed for direction pattern A and a scan executed for direction pattern B. The processing circuitry 18 sets the read ultrasound transmission/reception condition in the ultrasound transmission circuitry 11.

Based on the set ultrasound transmission/reception condition, the ultrasound transmission circuitry 11 executes an ultrasound scan for direction pattern A within the imaging ROI (step S31).

Specifically, for example, the ultrasound transmission circuitry 11 transmits ultrasound pulses a plurality of times in the first direction of direction pattern A shown in FIG. 2. The ultrasound pulses transmitted from the ultrasound probe 20 to the subject P are sequentially reflected on the acoustic impedance discontinuous surface of the body tissue and the bloodstream of the subject P. The reflected wave signals of the ultrasound pulses undergo frequency shifts in relation to the velocity component of the moving body of the bloodstream or the cardiac wall, etc. The reflected wave signals are received at the ultrasound probe 20.

For example, the ultrasound reception circuitry 12 performs processing with respect to the reflected wave signals received by the ultrasound probe 20 so that the directivity matches the first direction of direction pattern A, and generates a reception signal. The generated reception signal is retained in, for example, a buffer (not shown).

In the same manner, the ultrasound transmission circuitry 11 transmits ultrasound pulses a plurality of times in each of the second to fifth directions of direction pattern A. The ultrasound reception circuitry 12 receives reflected wave signals of the transmitted ultrasound pulses via the ultrasound probe 20. For example, the ultrasound reception circuitry 12 performs processing with respect to the received reflected wave signals of the second to fifth directions so that the directivity thereof respectively matches the second to fifth directions of direction pattern A, and generates reception signals. The reception signals generated for the second to fifth directions of direction pattern A are retained in, for example, a buffer.

When a scan in the fifth direction of direction pattern A is executed, and a stand-by time Δt has elapsed, the ultrasound transmission circuitry 11 executes, based on the set ultrasound transmission/reception condition, an ultrasound scan for direction pattern B within the imaging ROI (step S32).

Specifically, for example, the ultrasound transmission circuitry 11 sequentially transmits ultrasound pulses a plurality of times in each of the first to fourth directions of direction pattern B shown in FIG. 2. The ultrasound reception circuitry 12 receives reflected wave signals of the transmitted ultrasound pulses via the ultrasound probe 20. For example, the ultrasound reception circuitry 12 performs processing with respect to the received reflected wave signals of the first to fourth directions so that the directivity thereof respectively matches the first to fourth directions of direction pattern B, and generates reception signals. The reception signals generated for the first to fourth directions of direction pattern B are retained in, for example, a buffer.

When a scan for the color Doppler method is executed, the processing circuitry 18 executes the Doppler processing function 183 (step S33).

Specifically, for example, by the Doppler processing function 183, the processing circuitry 18 suppresses signals (clutter signals) related to stationary tissues or slow-moving tissues by applying a wall filter with respect to the reception signals generated for the first direction of direction pattern A so that bloodstream-related signals can be extracted. The processing circuitry 18 performs autocorrelation processing with respect to the signal on which the filter processing is performed, and calculates the autocorrelation value. From the calculated autocorrelation value, the processing circuitry 18 calculates an average velocity and dispersion for each sampled value of the first direction of direction pattern A. The processing circuitry 18 also calculates the power for each sampled value of the first direction of direction pattern A from the signal on which the filter processing is performed. In this manner, Doppler raw data for the first direction of direction pattern A is generated.

The processing circuitry 18 executes the same processing with respect to the reception signals generated for each of the second to fifth directions of direction pattern A. In this manner, Doppler raw data for each of the second to fifth directions of direction pattern A is generated.

The processing circuitry 18 also executes the same processing with respect to the reception signals generated for the first to fourth directions of direction pattern B. In this manner, Doppler raw data for each of the first to fourth directions of direction pattern B is generated.

The processing circuitry 18 also applies a predetermined weight to each of the signals of direction pattern A and direction pattern B on which the filter processing is performed, and combines them. For example, the processing circuitry 18 applies a predetermined weight to each of the signals of the first direction of direction pattern A and the first direction of direction pattern B and combines them. In this manner, signals may be calculated from a direction between the first direction of direction pattern A and the first direction of direction pattern B. In the same manner, for example, the processing circuitry 18 applies a predetermined weight to each of the signals of the other directions of direction pattern A and the other directions of direction pattern B and combines them. In this manner, signals may be calculated from direction pattern C, which is different from direction Patterns A and B. The processing circuitry 18 executes autocorrelation processing and arithmetic processing with respect to the reception signals generated for each direction belonging to direction pattern C, and calculates an average velocity, dispersion, and power for each sampled value of each direction belonging to direction pattern C. In this manner, Doppler raw data for each direction belonging to direction pattern C is generated.

Figure 4:
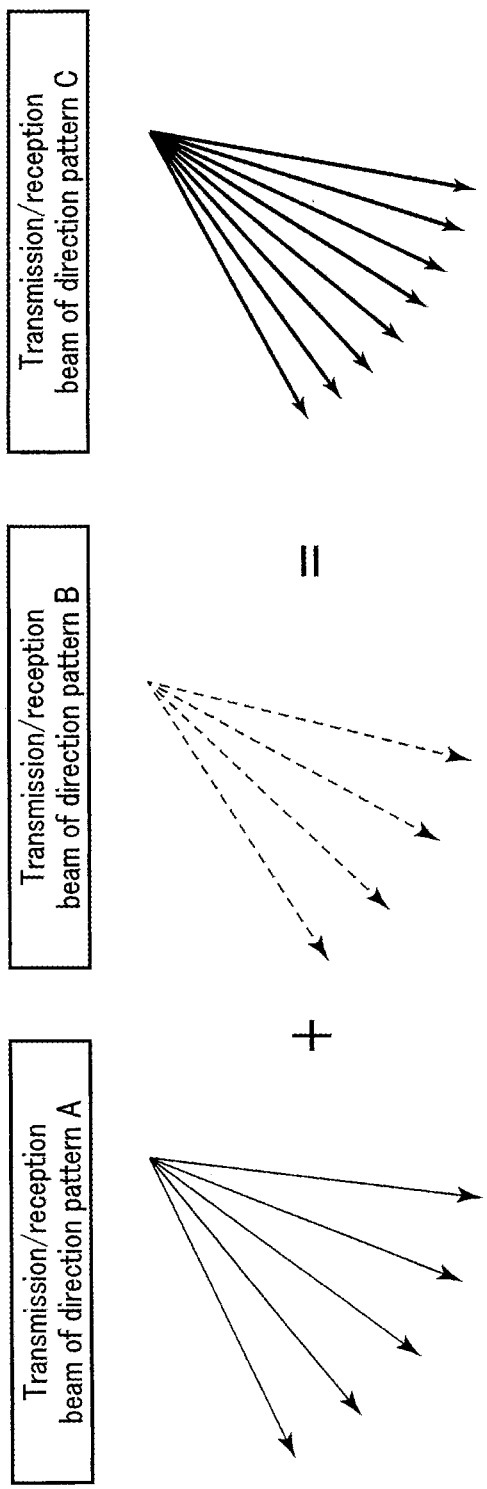
FIG. 4 is a diagram showing transmission/reception beams of direction patterns A and B, and a transmission/reception beam of direction pattern C prepared for simulation based on signals of direction patterns A and B.

FIG. 4 is a schematic diagram showing an example of transmission/reception beams of direction patterns A and B, and a transmission/reception beam of direction pattern C prepared for simulation based on the signals of direction patterns A and B. As shown in FIG. 4, transmission/reception beams are formed in a plurality of directions belonging to direction pattern A and a plurality of directions belonging to direction pattern B. By combining the signals relating to a plurality of directions belonging to direction patterns A and B, signals relating to direction pattern C may be calculated. In other words, transmission/reception beams of direction pattern C are formed in the manner expressed by a bold solid line in FIG. 4.

When the Doppler raw data is generated for direction patterns A, B, and C, the processing circuitry 18 executes the image generation function 184 (step S34).

Specifically, for example, by the image generation function 184, the processing circuitry 18 executes a raw-pixel conversion on the Doppler raw data for direction patterns A, B, and C to generate Doppler image data for the bloodstream information in the imaging ROI.

FIG. 5 is a schematic diagram showing an example of a scanning line direction realized by the transmission/reception beams of direction patterns A, B, and C. In this manner, the examination can be performed based on transmission/reception beams with a higher density than those formed only by direction patterns A and B.

In the bloodstream imaging mode, for example, a B-mode scan is performed in parallel with a color Doppler scan. For example, the processing circuitry 18 reads, from the internal storage 13, an ultrasound transmission/reception condition for the B-mode scan based on the scan sequence. The processing circuitry 18 sets the read ultrasound transmission/reception condition in the ultrasound transmission circuitry 11. The ultrasound transmission circuitry 11 transmits an ultrasound wave from the ultrasound probe 20 to the subject P based on the set ultrasound transmission/reception condition.

The ultrasound wave transmitted from the ultrasound probe 20 to the subject P is sequentially reflected by acoustic impedance discontinuous surfaces in the body tissue of the subject P, and is received at the ultrasound probe 20 as a reflected wave signal. The ultrasound reception circuitry 12 performs various types of processing on the reflected wave signal received by the ultrasound probe 20 to generate a reception signal. The generated reception signal is retained in, for example, a buffer.

When the B-mode scan is executed, by the B-mode processing function 182, the processing circuitry 18 generates B-mode data for the scan area based on the reception signal retained in the buffer.

When the B-mode data is generated, by the image generation function 184, the processing circuitry 18 generates B-mode image data based on the B-mode data. When the Doppler image data and the B-mode image data are generated, the processing circuitry 18 generates ultrasound image data in which the image data is combined.

When the ultrasound image data is generated, by the display control function 185, the processing circuitry 18 displays an image based on the generated ultrasound image data on the display device 40 (step S35).

The processing circuitry 18 then determines whether or not to continue the measurement (step S36). For example, the processing circuitry 18 ends the processing when it receives an instruction to end the measurement from the operator via the input interface 15, or an operation to end the measurement is input to the ultrasound probe 20 (step S36, No). In the case where the above input is not made (step S36, Yes), the processing circuitry 18 repeats the processing from step S31.

In the above manner, in the first embodiment, the ultrasound transmission circuitry 11 forms transmission beams in a plurality of directions belonging to direction pattern (direction group) A. The ultrasound transmission circuitry 11 forms transmission beams in a plurality of directions belonging to direction pattern B after a predetermined time has elapsed from performing the scan for direction pattern A. The ultrasound reception circuitry 12 forms at least one reception beam in response to every transmission beam. The processing circuitry 18 applies a wall filter to the reception signals obtained by performing scans for direction patterns A and B, and calculates the bloodstream information based on the filtered signals. The processing circuitry 18 is configured to generate the image data based on the calculated bloodstream information. In this manner, since transmission beams of different directions may be formed between direction patterns A and B, sensitivity differences which may occur in accordance with the direction in which the bloodstream flows may be suppressed. Furthermore, since there is a predetermined time difference between the scan of direction pattern A and the scan of direction pattern B, and the arrangement of the scatterers in the blood changes, the influence from spatial amplitude fluctuations of the received ultrasound signals caused by the arrangement patterns of the scatterers in the blood may be suppressed.

In the first embodiment, an example of a case in which the filter coefficient of the wall filter in the filter processing is fixed is explained. However, the filter coefficient of the wall filter does not have to be fixed. For example, the wall filter may be an adaptive filter that changes the coefficient in accordance with the input signal using eigenvalue decomposition or singular value decomposition, etc.

Figure 6:
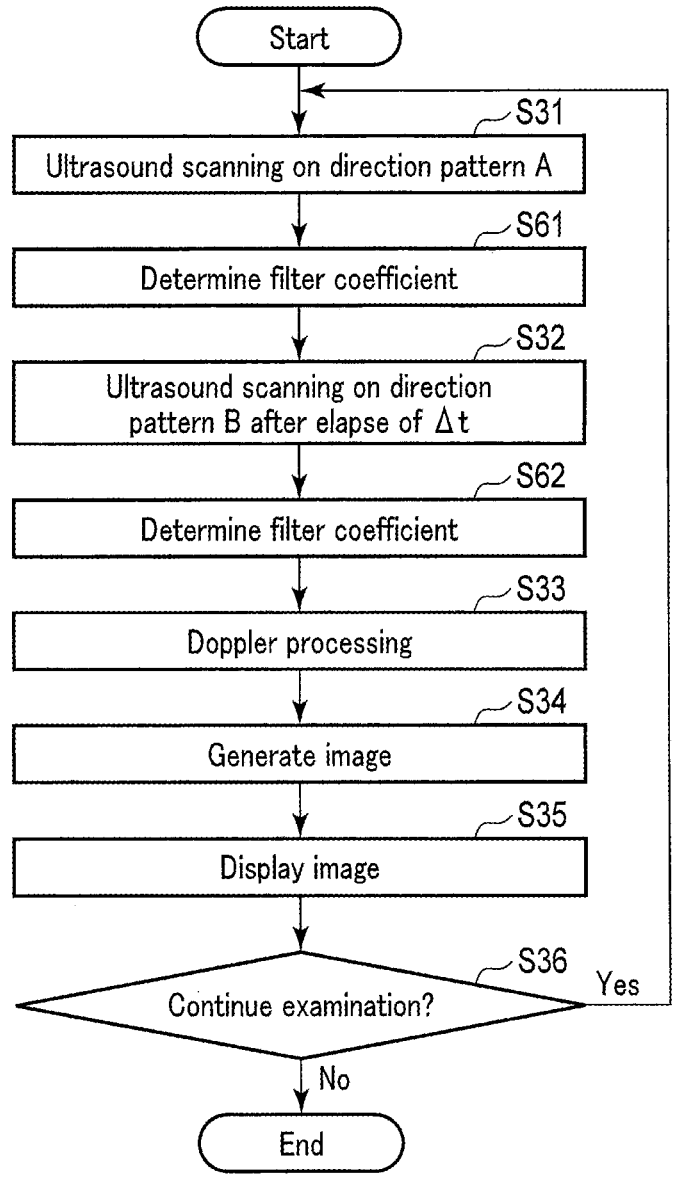
FIG. 6 is a flowchart showing operations of the processing circuitry in a case where a wall filter is an adaptive filter.

FIG. 6 is a flowchart showing an example of operations of the processing circuitry 18 in a case where the wall filter is an adaptive filter. In FIG. 6, when an ultrasound scan is executed for direction pattern A (step S31), the processing circuitry 18 determines a filter coefficient for a reception signal generated by this scan (step S61). For example, the processing circuitry 18 calculates a characteristic vector from a correlation matrix relating to the reception signal, and calculates a coefficient to be used for the wall filter from the calculated characteristic vector.

When an ultrasound scan is executed on direction pattern B (step S32), the processing circuitry 18 determines a filter coefficient for a reception signal generated by this scan (step S62).

When the filter coefficient for the reception signal of direction pattern B is determined, the processing circuitry 18 uses the determined filter coefficient to execute the Doppler processing function 183 in step S33.

In this manner, by adopting an adaptive wall filter in which the filter coefficient is changeable, a clutter signal can be suppressed more efficiently. Furthermore, by obtaining a filter coefficient that is adaptive to each of the reception signal groups having different transmission direction patterns, differences will occur in a velocity range value, etc., which will enhance independence among the bloodstream Doppler signals. Therefore, by combining these reception signals, it is possible to enhance the effect of suppressing irregularities in the amplitude of the bloodstream signals caused by interference.

In the first embodiment, an example of a case in which signals of direction pattern C, which is different from direction patterns A and B, are generated based on the signals of direction patterns A and B is explained. However, the signals of direction pattern C do not have to be generated.

In the case where the signals of direction pattern C are not generated, for example, the processing circuitry 18 generates, by the image generation function 184, the Doppler image data relating to the bloodstream information in the imaging ROI by executing the raw-pixel conversion on the Doppler raw data for direction patterns A and B.

Furthermore, in the case where the signals of direction pattern C are not generated, for example, the processing circuitry 18 may execute, by the Doppler processing function 183, smoothing filtering processing between the signals of direction pattern A and the signals of direction pattern B. Specifically, for example, the processing circuitry 18 obtains a value relating to a sampled value of interest by using a weighted average of peripheral data including sampled values of direction patterns A and B. Here, the filter coefficients of the smoothing filter may be set as needed. For example, the smoothing filter may be a Gaussian filter.

Furthermore, in the first embodiment, an example of generating Doppler image data relating to the bloodstream information by executing the raw-pixel conversion on the Doppler raw data for direction patterns A, B, and C is explained. However, the Doppler image data is not limited to being based on the Doppler raw data relating to direction patterns A, B, and C. For example, the processing circuitry 18 may generate the Doppler image data based on the Doppler raw data relating to direction pattern C.

Specifically, for example, in step S34 of FIG. 3, the processing circuitry 18 executes a raw-pixel conversion on the Doppler raw data relating to direction pattern C to generate Doppler image data for the bloodstream information in the imaging ROI.

Furthermore, in the first embodiment, an example of a case in which the Doppler processing function 183 combines the signals relating to direction patterns A and B to generate the signals relating to direction pattern C is explained. However, the signals relating to direction patterns A and B are not limited to being combined by the Doppler processing function 183. The signals of direction patterns A and B may be combined at any time. For example, the signals may be combined by the image generation function 184.

Specifically, for example, by the image generation function 184, the processing circuitry 18 combines the Doppler raw data relating to direction patterns A and B to calculate the Doppler raw data relating to direction pattern C, which is different from direction patterns A and B. That is, the image generation function 184 may also be an example of a combining unit. The processing circuitry 18 executes a raw-pixel conversion on the Doppler raw data relating to direction patterns A, B, and C to generate the Doppler image data for the bloodstream information in the imaging ROI.

The matter of combining the signals relating to direction patterns A and B is not limited to digital signals. For example, RF signals, baseband signals, or signals obtained after envelope detection processing may be combined.

Second Embodiment

In the first embodiment, an example of a case in which the direction pattern and time difference $\Delta t$ are set in advance is explained. In a second embodiment, a case in which a direction pattern and time difference $\Delta t$ are determined by performing a scan in advance will be explained.

Figure 7:
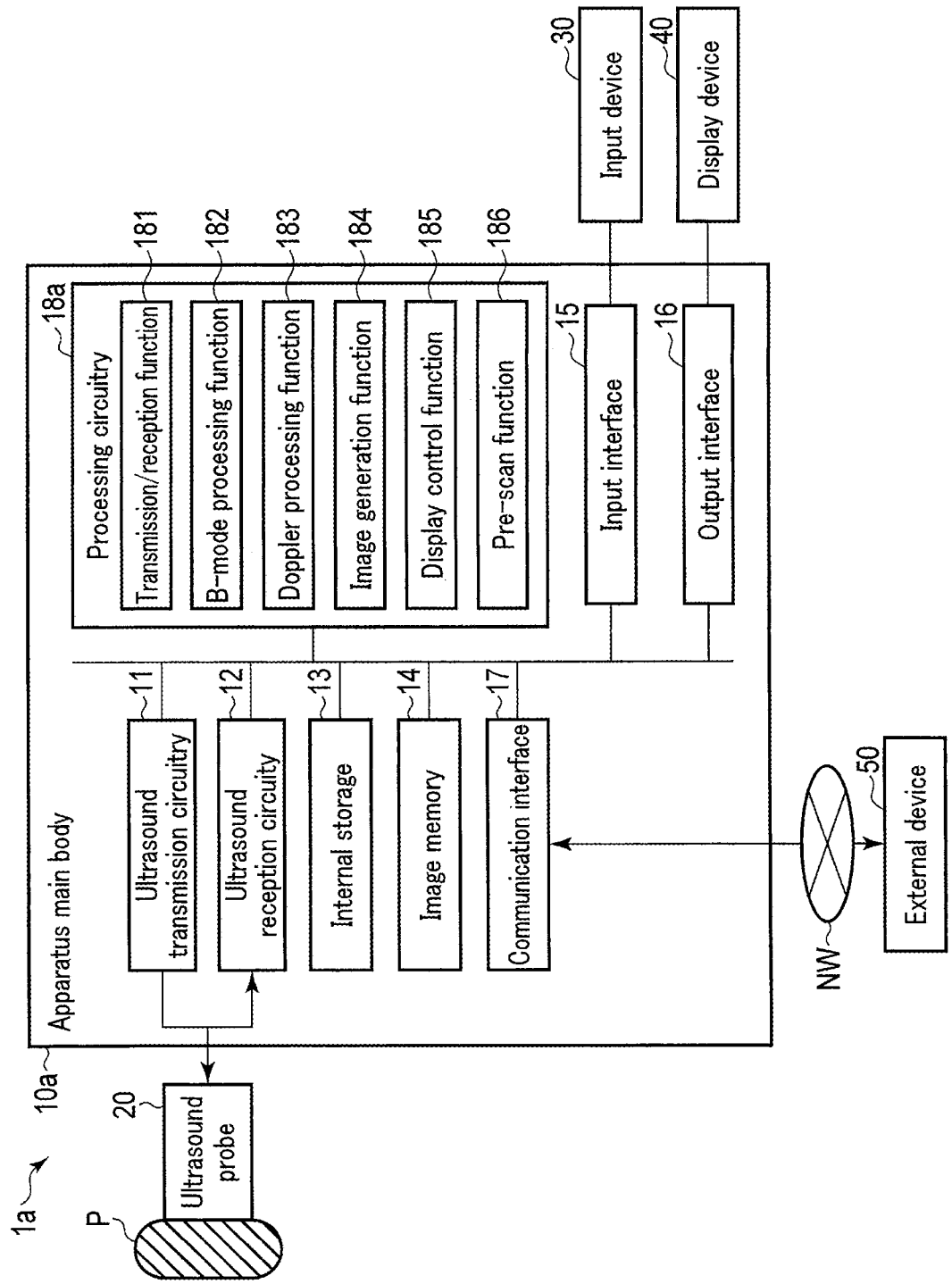
FIG. 7 is a block diagram showing a functional configuration of an ultrasound diagnostic apparatus according to a second embodiment.

FIG. 7 is a block diagram showing an example of a functional configuration of an ultrasound diagnostic apparatus 1a according to the second embodiment. The ultrasound diagnostic apparatus 1a shown in FIG. 7 includes an apparatus main body 10a and an ultrasound probe 20. The apparatus main body 10a is connected to an input device 30 and a display device 40. The apparatus main body 10a is connected to an external device 50 via a network NW.

The apparatus main body 10a generates an ultrasound image based on a reflected wave signal received by the ultrasound probe 20. The apparatus main body 10a includes ultrasound transmission circuitry 11, ultrasound reception circuitry 12, internal storage 13, an image memory 14, an input interface 15, an output interface 16, a communication interface 17, and processing circuitry 18a.

The processing circuitry 18a is, for example, a processor that functions as a nerve center of the ultrasound diagnostic apparatus 1a. The processing circuitry 18a executes a program stored in the internal storage 13, thereby realizing the functions corresponding to the program. The processing circuitry 18a may include, for example, a transmission/reception function 181, B-mode processing function 182, Doppler processing function 183, image generation function 184, display control function 185, and pre-scan function 186. The present embodiment explains a case in which a single processor realizes the transmission/reception function 181, B-mode processing function 182, Doppler processing function 183, image generation function 184, display control function 185, and pre-scan function 186. However, the embodiment is not limited thereto. For example, processing circuitry may be configured by combining a plurality of independent processors, and the transmission/reception function 181, B-mode processing function 182, Doppler processing function 183, image generation function 184, display control function 185, and pre-scan function 186 may be realized by executing programs of each processor. Dedicated hardware circuitry capable of executing each function may be incorporated.

The pre-scan function 186 serves to control a scan for determining a direction pattern and time difference $\Delta t$ in advance, and is an example of a preliminary treatment controller. With the pre-scan function 186, the processing circuitry 18 controls the transmission of ultrasound waves by the ultrasound transmission circuitry 11 and the reception of reflected wave signals by the ultrasound reception circuitry 12, in accordance with the information for the pre-scan read from the internal storage 13. The processing circuitry 18 determines the direction pattern and the time difference $\Delta t$ based on the reception signals acquired by the pre-scan.

An example of measurement processing performed by the ultrasound diagnostic apparatus 1a configured in the above manner will now be explained.

Figure 8:
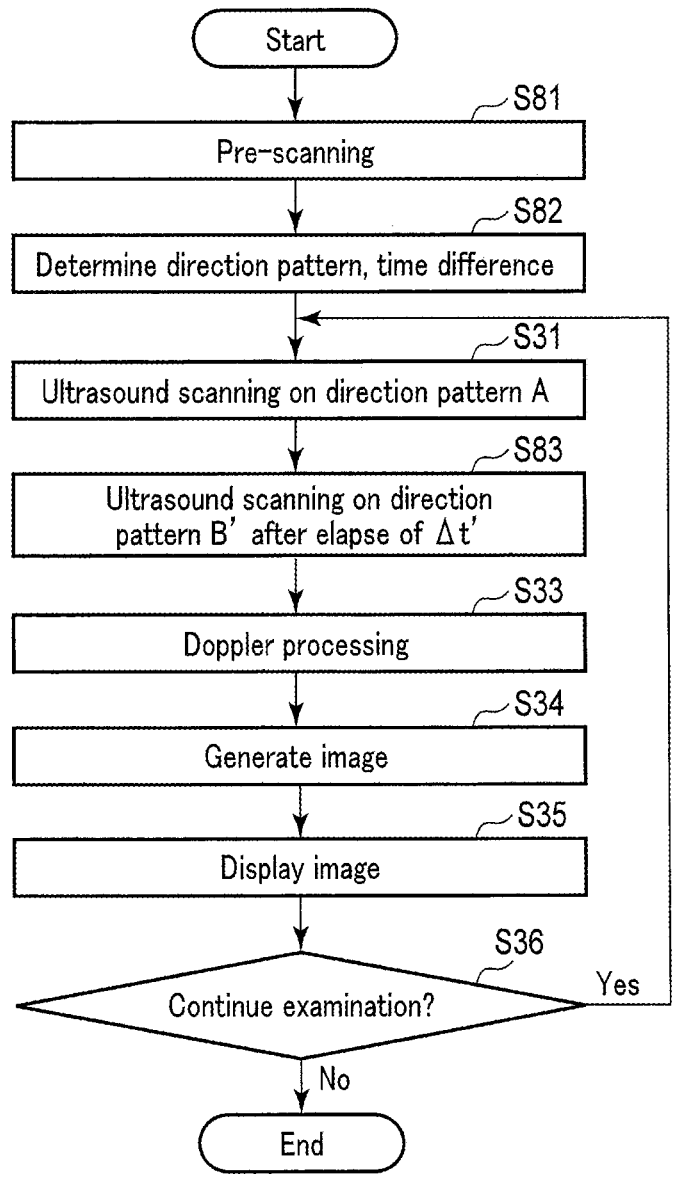
FIG. 8 is a flowchart showing operations of processing circuitry when displaying an ultrasound image on a display device of the ultrasound diagnostic apparatus shown in FIG. 7.

FIG. 8 is a flowchart showing an example of operations of the processing circuitry 18a when displaying an ultrasound image on the display device 40 of the ultrasound diagnostic apparatus 1a shown in FIG. 7. In the explanation of FIG. 8, an imaging ROI for generating Doppler image data is assumed to be set in a scan area via the input interface 15.

First, an operator selects, for example, a bloodstream imaging mode, and inputs a start instruction to start the selected bloodstream imaging mode via the input interface 15. When the start instruction to start the bloodstream imaging mode is input, the processing circuitry 18a executes the pre-scan function 186.

With the pre-scan function 186, the processing circuitry 18a first executes a scan on the imaging ROI (step S81). Specifically, for example, the processing circuitry 18a reads an ultrasound transmission/reception condition for the pre-scan from the internal storage 13. In the explanation relating to FIG. 8, the ultrasound transmission/reception condition includes, for example, information for forming transmission beams in direction pattern A as a default. The processing circuitry 18*a* sets the read ultrasound transmission/reception condition in the ultrasound transmission circuitry 11.

Based on the set ultrasound transmission/reception condition, the ultrasound transmission circuitry 11 sequentially transmits ultrasound pulses a plurality of times in each direction belonging to direction pattern A within the imaging ROI. The ultrasound reception circuitry 12 receives reflected wave signals of the transmitted ultrasound pulses via the ultrasound probe 20. The ultrasound reception circuitry 12 performs processing with respect to the received reflected wave signals of each direction so that, for example, the directivity thereof respectively matches each direction of direction pattern A, and generates reception signals.

When a scan is executed, by the Doppler processing function 183, the processing circuitry 18*a* generates Doppler data from the generated reception signals. When the Doppler data is generated, by the image generation function 184, the processing circuitry 18*a* generates Doppler image data in which bloodstream information is visualized.

The processing circuitry 18*a* analyzes the generated Doppler image data to detect luminance irregularities included in the Doppler image data. Specifically, for example, the processing circuitry 18*a* analyzes the generated Doppler image data to calculate an index for detecting the luminance irregularity. The luminance irregularity indicates an area in which luminance is unnaturally low compared to the luminance of a surrounding area. The index for detecting the luminance irregularity is an index for evaluating spatial evenness of a bloodstream signal intensity, for which, for example, a luminance dispersion/average is used. According to this index, when an index value is high, the luminance is highly irregular in an image. However, the index is not limited thereto.

The processing circuitry 18*a* determines the direction pattern and the time difference based on the calculated index (step S82). Specifically, for example, the processing circuitry 18*a* determines the direction pattern such that the transmission beams pass through an area with a high index value, and are formed in a density in accordance with the level of the index value. Furthermore, the processing circuitry 18*a* determines the time difference in accordance with the level of the index value. The direction pattern and the time difference may be associated with the index value and a position of an area with a high index value, and have a plurality of pieces of candidate data stored in the internal storage 13 in advance. Furthermore, the direction pattern and the time difference may be generated appropriately in accordance with the calculated index value and the position of an area with a high index value.

When the direction pattern and the time difference are determined, the processing circuitry 18*a* executes the transmission/reception function 181. With the transmission/reception function 181, the processing circuitry 18*a* reads, for example, a scan sequence for the bloodstream imaging mode from the internal storage 13. The processing circuitry 18*a* executes a scan based on the read scan sequence.

For example, based on the scan sequence, the processing circuitry 18*a* reads an ultrasound transmission/reception condition for a color Doppler method from the internal storage 13. In the explanation relating to FIG. 8, the ultrasound transmission/reception condition includes, for example, information for forming transmission beams in direction pattern A as a default. The ultrasound transmission/reception condition also includes, for example, information for forming transmission beams in direction pattern B' determined by the pre-scan, and information relating to a time difference determined by the pre-scan. The processing circuitry 18*a* sets the read ultrasonic transmission/reception condition in the ultrasound transmission circuitry 11.

Based on the set ultrasound transmission/reception condition, the ultrasound transmission circuitry 11 executes an ultrasound scan for direction pattern A within the imaging ROI (step S31).

Specifically, for example, based on the set ultrasound transmission/reception condition, the ultrasound transmission circuitry 11 sequentially transmits ultrasound pulses a plurality of times in each direction belonging to direction pattern A within the imaging ROI. The ultrasound reception circuitry 12 receives reflected wave signals of the transmitted ultrasound pulses via the ultrasound probe 20. The ultrasound reception circuitry 12 performs processing with respect to the received reflected wave signals of each direction so that, for example, the directivity thereof respectively matches each direction of direction pattern A, and generates reception signals.

When a scan is executed for direction pattern A, and a determined time $\Delta t'$ has elapsed, based on the set ultrasound transmission/reception condition, the ultrasound transmission circuitry 11 executes an ultrasound scan for direction pattern B' within the imaging ROI (step S83).

Specifically, for example, the ultrasound transmission circuitry 11 sequentially transmits ultrasound pulses a plurality of times in each direction belonging to direction pattern B'. The ultrasound reception circuitry 12 receives reflected wave signals of the transmitted ultrasound pulses via the ultrasound probe 20. The ultrasound reception circuitry 12 performs processing with respect to the received reflected wave signals of each direction so that, for example, the directivity thereof respectively matches each direction of direction pattern B', and generates reception signals.

When a scan for the color Doppler method is executed, the processing circuitry 18*a* executes the Doppler processing function 183 (step S33), and generates Doppler raw data for each direction belonging to direction patterns A and B'. The processing circuitry 18*a* also applies a predetermined weight to each of the signals of direction pattern A and direction pattern B' and combines them to calculate signals from direction pattern C', which is different from direction patterns A and B'. The processing circuitry 18*a* executes autocorrelation processing and arithmetic processing with respect to the reception signals generated for each direction belonging to direction pattern C', and generates Doppler raw data for each direction belonging to direction pattern C'.

When the Doppler raw data is generated for direction patterns A, B', and C', the processing circuitry 18*a* executes the image generation function 184 (step S34), and generates Doppler image data in the imaging ROI based on the Doppler raw data relating to direction patterns A, B', and C'. When B-mode image data is generated by a B-mode scan executed in parallel with the color Doppler scan, the processing circuitry 18*a* generates ultrasound image data in which the Doppler image data and the B-mode image data are combined.

When the ultrasound image data is generated, by the display control function 185, the processing circuitry 18*a* displays an image based on the generated ultrasound image data on the display device 40 (step S35).

The processing circuitry 18*a* then determines whether or not to continue the measurement (step S36). In a case where an instruction to end the measurement is given (step S36, No), the processing circuitry 18*a* ends the processing. In the case where no instruction is given to end the measurement (step S36, Yes), the processing circuitry 18*a* repeats the processing from step S31.

In the above manner, in the second embodiment, by the pre-scan function 186, the processing circuitry 18a is configured to determine the direction pattern and the time difference based on the reception signals acquired by the pre-scan. Therefore, in a case where there is an area with spatially uneven bloodstream signal intensity, a direction pattern and time difference suitable for such an area can be adopted, thereby allowing the influence of a sensitivity difference which may occur in accordance with the direction in which the bloodstream flows and the influence of scattered ultrasound waves caused by the scatterers in the blood to be efficiently suppressed.

In the second embodiment, an example of a case in which one direction pattern is determined in a pre-scan is explained. However, the number of direction patterns determined by the pre-scan is not limited to one. For example, two or more direction patterns may be determined.

For example, in a case where two direction patterns are determined, the processing circuitry 18a forms transmission/reception beams in a direction belonging to one of the direction patterns determined in an initial ultrasound scan. The processing circuitry 18a then forms transmission/reception beams in a direction belonging to the other direction of the determined direction patterns in the next ultrasound scan.

Furthermore, in the second embodiment, an example of a case in which one direction pattern determined in the pre-scan is utilized in the second ultrasound scan is explained. However, the direction pattern determined by the pre-scan may be utilized in the initial ultrasound scan.

Furthermore, in the second embodiment, the pre-scan is explained as a scan independent of the initial ultrasound scan utilizing direction pattern A which is set as a default. However, the pre-scan may also be at least a part of the initial ultrasound scan. For example, the processing circuitry 18a may analyze the Doppler image data generated based on the reception signal acquired in step S31 shown in FIG. 8, and calculate an index for evaluating spatial evenness of the bloodstream signal intensity. The processing circuitry 18a then determines the direction pattern and the time difference based on the calculated index. The pre-scan may be executed every time the ultrasound scan utilizing direction pattern A is executed, or may be executed at a predetermined cycle.

Furthermore, in the second embodiment, an example of a case in which a pre-scan is executed only once when starting an examination is explained. However, the pre-scan is not limited to being executed only once when starting the examination. For example, the processing circuitry 18a may execute the pre-scan at a predetermined cycle. That is, the direction pattern and the time difference may vary for every predetermined cycle.

Furthermore, in the second embodiment, an example of a case in which direction patterns across the entire imaging ROI are determined by a pre-scan is explained. However, the direction patterns determined by the pre-scan are not limited to those obtained across the entire imaging ROI. The processing circuitry 18a may determine direction patterns including only directions of areas in which the bloodstream signal intensity is spatially uneven, that is, areas in which luminance irregularity is detected.

Therefore, since the scan range of the second ultrasound scan becomes narrower, the frame rate improves.

(First Modification) In the first embodiment mentioned above, a method of forming transmission/reception beams of direction pattern C based on signals of direction patterns A and B was explained. In a first modification, a method of sequentially forming transmission/reception beams of direction pattern C based on signals of direction patterns A and B acquired in real time will be explained.

Figure 9:
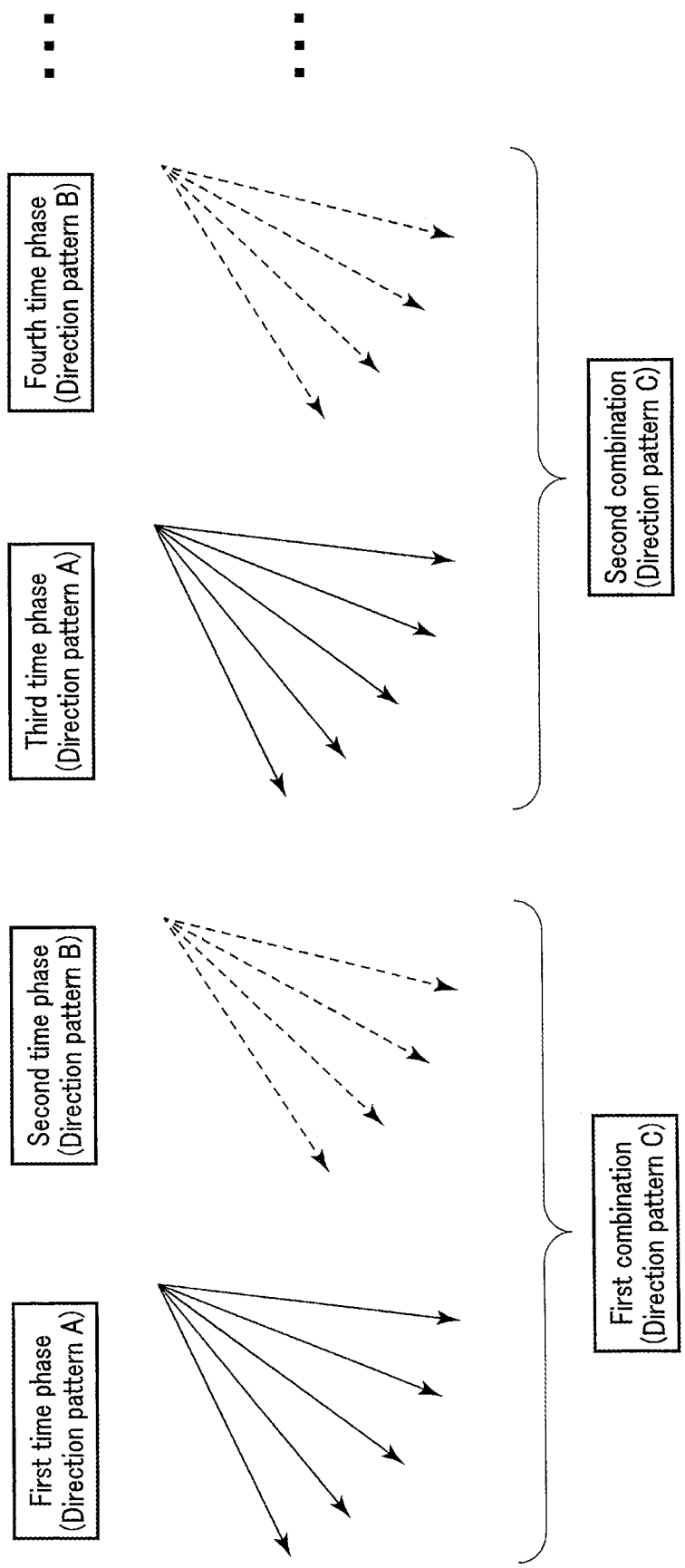
FIG. 9 is a diagram showing transmission/reception beams of direction pattern C prepared in real time based on signals of direction patterns A and B in a first modification.

FIG. 9 is a diagram showing transmission/reception beams of direction pattern C prepared in real time based on signals of direction patterns A and B in the first modification. As shown in FIG. 9, transmission/reception beams are formed in a plurality of directions belonging to direction pattern A in a first phase, and transmission/reception beams are formed in a plurality of directions belonging to direction pattern B in a second time phase. By combining the signals relating to a plurality of directions belonging to direction patterns A and B corresponding to the first time phase and the second time phase, signals relating to direction pattern C may be calculated.

Subsequently, transmission/reception beams are formed in a plurality of directions belonging to direction pattern A in a third phase, and transmission/reception beams are formed in a plurality of directions belonging to direction Pattern B in a fourth time phase. By combining the signals relating to a plurality of directions belonging to direction patterns A and B corresponding to the third time phase and the fourth time phase, signals relating to direction pattern C may be calculated. Hereinafter, the above-mentioned processing is repeated.

In the above manner, in the first modification, a first combination is performed based on signals of direction pattern A in the first time phase and signals of direction pattern B in the second time phase, and a second combination is performed based on signals of direction pattern A in the third time phase and signals of direction pattern B in the fourth time phase. That is, in the first modification, every time both of the signals of direction pattern A and the signals of direction pattern B used for the combining are updated, the combining of direction pattern C is performed. Therefore, in the first modification, signals may be combined in real time.

(Second Modification)

In the first modification mentioned above, in order to form the transmission/reception beams of direction pattern C, both signals of direction patterns A and B acquired in real time were updated. However, it is not limited thereto. In a second modification, a method of updating one of the signals of direction patterns A and B acquired in real time to form transmission/reception beams of direction pattern C will be explained.

Figure 10:
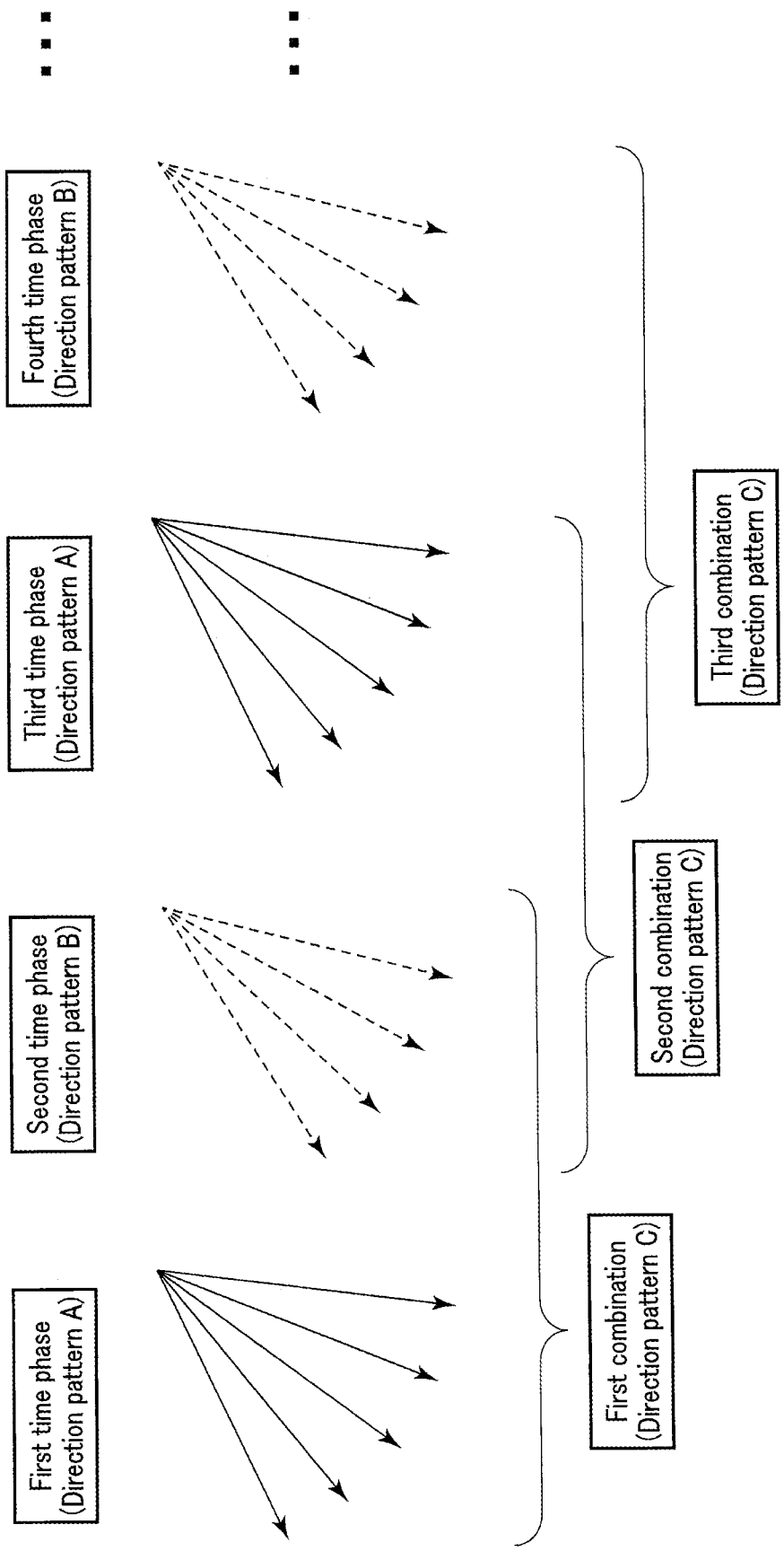
FIG. 10 is a diagram showing transmission/reception beams of direction pattern C prepared in real time based on signals of direction patterns A and B in a second modification.

FIG. 10 is a diagram showing transmission/reception beams of direction pattern C prepared in real time based on the signals of direction patterns A and B in the second modification. As shown in FIG. 10, transmission/reception beams are formed in a plurality of directions belonging to direction pattern A in a first time phase, and transmission/reception beams are formed in a plurality of directions belonging to direction pattern B in a second time phase. By combining the signals relating to a plurality of directions belonging to direction patterns A and B corresponding to the first time phase and the second time phase, signals relating to direction pattern C may be calculated.

Subsequently, transmission/reception beams are formed in a plurality of directions belonging to direction pattern A in a third time phase. By combining the signals relating to a plurality of directions belonging to direction patterns A and B corresponding to the second time phase and the third time phase, signals relating to direction pattern C may be calculated.

Furthermore, transmission/reception beams are formed in a plurality of directions belonging to direction pattern B in a fourth time phase. By combining the signals relating to a plurality of directions belonging to direction patterns A and B corresponding to the third time phase and the fourth time phase, signals relating to direction pattern C may be calculated. Hereinafter, the above-mentioned processing is repeated.

In the above manner, in the second modification, a first combination is performed based on signals of direction pattern A in the first time phase and signals of direction pattern B in the second time phase, a second combination is performed based on signals of direction Pattern B in the second time phase and signals of direction pattern A in the third time phase, and a third combination is performed based on signals of direction pattern A in the third time phase and signals of direction pattern B in the fourth time phase. That is, in the second modification, every time one of the signals of direction pattern A or B used for the combining are updated, the combining of direction pattern C is performed. Therefore, in the second modification, a frame rate can be further improved than in the first modification.

(Third Modification)

In each of the embodiments and modifications mentioned above, methods of combining signals acquired from two different direction patterns were explained. However, it is not limited thereto. For example, signals acquired from three or more different direction patterns may be combined. The number of direction patterns may be determined by, for example, a pre-scan. In the following, as an example, a method of combining signals acquired from three different direction patterns will be explained with reference to FIG. 11.

FIG. 11 is a diagram showing directions in which transmission beams are formed in a third modification. According to FIG. 11, transmission beams are sequentially formed from a first direction to a fifth direction belonging to direction pattern a. Transmission beams are also sequentially formed from a first direction to a fourth direction belonging to direction pattern b. Transmission beams are also sequentially formed from a first direction to a fourth direction belonging to direction pattern c. The five directions belonging to direction pattern a, the four directions belonging to direction pattern b, and the four directions belonging to direction pattern c are respectively different directions.

The number of a plurality of directions belonging to each of direction patterns a, b, and c is not limited to the above. For example, the number of the plurality of directions belonging to each of direction patterns a, b, c may all be the same or may each be different. The plurality of directions belonging to each of direction patterns a, b, and c may also be increased or reduced in accordance with a frame rate.

Furthermore, a stand-by time of $\Delta t1$ exists between reception of a reflected wave signal with respect to a transmission beam formed in the last direction belonging to direction pattern a, that is, the fifth direction of direction pattern a, and formation of a transmission beam in the first direction belonging to direction pattern b, that is, the first direction of direction pattern b. Furthermore, a stand-by time of $\Delta t2$ exists between reception of a reflected wave signal with respect to a transmission beam formed in the last direction belonging to direction pattern b, that is, the fourth direction of direction pattern b, and formation of a transmission beam in the first direction belonging to direction pattern c, that is, the first direction of direction pattern c.

A time difference $\Delta t1$ and a time difference $\Delta t2$ may be the same value or different values, may be set in advance, or may be determined by a pre-scan.

In the manner mentioned above, in the third modification, signals acquired from three different direction patterns can be combined. Therefore, in the third modification, imaging conditions can be determined more flexibly than in each of the embodiments or each of the modifications mentioned above.

According to at least one of the above-described embodiments, the ultrasound diagnostic apparatuses 1 and 1a are able to suppress the luminance irregularities in the bloodstream image.

The word "processor" in the embodiment may refer to circuitry such as a central processing unit (CPU), graphics processing unit (GPU), or application specific integrated circuit (ASIC); or a programmable logic device (e.g., simple programmable logic device (SPLD), complex programmable logic device (CPLD), or field programmable gate array (FPGA)). The processor realizes functions by reading and executing programs stored in the memory circuitry. Instead of storing the programs in the memory circuitry, the programs may be directly incorporated in the circuitry of the processor. In this case, the processor realizes the functions by reading and executing the programs incorporated in the circuitry. Each processor of the above embodiments is not limited to a single circuit configured for each processor, but may be configured as a single processor in which a plurality of independent circuits are combined, and realize the functions thereof. Furthermore, the structural components of each of the above embodiments may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus, comprising:
processing circuitry configured to
form a first transmission beam in each of a first plurality of directions belonging to a first direction group, the first transmission beam being formed multiple times in each of the first plurality of directions;
form a first reception beam for each of the first transmission beams so as to perform a first scan;
form a second transmission beam in each of a second plurality of directions belonging to a second direction group, the second transmission beam being formed multiple times in each of the second plurality of directions, after an elapse of a predetermined time from performing the first scan for the first direction group, wherein one of the second plurality of directions is interposed between an adjacent pair of the first plurality of directions and the predetermined time is based on a bloodstream velocity;
form a second reception beam for each of the second transmission beams so as to perform a second scan;
apply a wall filter to first reception signals obtained by the first reception beams to generate first filtered reception signals, and to second reception signals obtained by the second reception beams to generate second filtered reception signals;
calculate bloodstream information based on the generated first and second filtered reception signals; and generate image data based on the calculated bloodstream information.

2. The ultrasound diagnostic apparatus according to claim 1, wherein the processing circuitry is further configured to adaptively determine a filter coefficient of the wall filter in accordance with the first reception signals obtained by the first reception beams and the second reception signals obtained by the second reception beams.

3. The ultrasound diagnostic apparatus according to claim 1, wherein the processing circuitry is further configured to:
calculate a third reception signal obtained by a third reception beam corresponding to a third transmission beam formed in each of a third plurality of directions belonging to a third direction group by combining the first reception signal obtained by the first reception beam and the second reception signal obtained by the second reception beam; and
generate the image data based on bloodstream information calculated from the third reception signal.

4. The ultrasound diagnostic apparatus according to claim 1, wherein the processing circuitry is further configured to:
calculate a third reception signal obtained by a third reception beam corresponding to a third transmission beam formed in each of a third plurality of directions belonging to a third direction group by combining the first reception signal obtained by the first reception beam and the second reception signal obtained by the second reception beam; and
generate the image data based on bloodstream information calculated from the first, second, and third reception signals.

5. The ultrasound diagnostic apparatus according to claim 1, wherein the processing circuitry is further configured to:
determine at least one of the first direction group and the second direction group based on a reception signal obtained by a pre-scan; and
determine the predetermined time based on the reception signal obtained by the pre-scan.

6. The ultrasound diagnostic apparatus according to claim 1, wherein the processing circuitry is further configured to:
determine, based on a reception signal obtained by a pre-scan, a direction group including at least a direction directed to an area in which bloodstream signal intensity is spatially uneven as the first direction group or the second direction group; and
determine the predetermined time based on the reception signal obtained by the pre-scan.

7. The ultrasound diagnostic apparatus according to claim 5, wherein the processing circuitry is further configured to execute the pre-scan at a pre-set cycle.

8. The ultrasound diagnostic apparatus according to claim 6, wherein the processing circuitry is further configured to execute the pre-scan at a pre-set cycle.

9. The ultrasound diagnostic apparatus according to claim 1, wherein the processing circuitry is further configured to:
determine the second direction group based on a reception signal obtained by performing a scan for the first direction group; and
determine the predetermined time based on the reception signal obtained by performing the scan for the first direction group.

10. The ultrasound diagnostic apparatus according to claim 1, wherein the processing circuitry is further configured to:
form a third transmission beam in a third plurality of directions belonging to the first direction group after an elapse of the predetermined time from performing the second scan for the second direction group;
form a third reception beam for each of the third transmission beams;
form a fourth transmission beam in a fourth plurality of directions belonging to the second direction group after an elapse of the predetermined time from performing a scan for the immediately preceding first direction group;
form a fourth reception beam for each of the fourth transmission beams; and
apply the wall filter to reception signals obtained by the third reception beams and the fourth reception beams.

11. The ultrasound diagnostic apparatus according to claim 1, wherein the processing circuitry is further configured to:
form a third transmission beam in a third plurality of directions belonging to the first direction group after an elapse of the predetermined time from performing the second scan for the second direction group;
form a third reception beam for each of the third transmission beams; and
apply the wall filter to reception signals obtained by the second reception beams and the third reception beams.

12. The ultrasound diagnostic apparatus according to claim 1, wherein the processing circuitry is further configured to:
form a third transmission beam in a third plurality of directions belonging to a third direction group after an elapse of the predetermined time from performing the second scan for the second direction group;
form a third reception beam for each of the third transmission beams; and
apply the wall filter to reception signals obtained by the first reception beams and the third reception beams.

13. The ultrasound diagnostic apparatus according to claim 1, wherein the predetermined time is a time required for an arrangement of scatterers included in blood to change.

14. The ultrasonic diagnostic apparatus of claim 1, wherein the processing circuitry is further configured to form the first transmission beam the multiple times in each of the first plurality of directions prior to forming the second transmission beam for a first time.

15. An examination method, comprising:
forming a first transmission beam in each of a first plurality of directions belonging to a first direction group, the first transmission beam being formed multiple times in each of the first plurality of directions;
forming a first reception beam for each of the first transmission beams so as to perform a first scan;
forming a second transmission beam in each of a second plurality of directions belonging to a second direction group, the second transmission beam being formed multiple times in each of the second plurality of directions, after an elapse of a predetermined time from performing the first scan for the first direction group, wherein one of the second plurality of directions is interposed between an adjacent pair of the first plurality of directions and the predetermined time is based on a bloodstream velocity;
forming a second reception beam for each of the second transmission beams so as to perform a second scan;
applying a wall filter to first reception signals obtained by the first reception beams to generate first filtered reception signals, and to second reception signals obtained by the second reception beams to generate second filtered reception signals;

calculating bloodstream information based on the generated first and second filtered reception signals; and generating image data based on the calculated bloodstream information.

\* \* \* \* \*